(12) United States Patent
Koiso

(10) Patent No.: US 11,607,111 B2
(45) Date of Patent: Mar. 21, 2023

(54) MEDICAL SIGNAL PROCESSING APPARATUS AND MEDICAL OBSERVATION SYSTEM

(71) Applicant: Sony Olympus Medical Solutions Inc., Tokyo (JP)

(72) Inventor: Manabu Koiso, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 18 days.

(21) Appl. No.: 17/477,543

(22) Filed: Sep. 17, 2021

(65) Prior Publication Data

US 2022/0005166 A1  Jan. 6, 2022

Related U.S. Application Data

(63) Continuation of application No. 15/808,106, filed on Nov. 9, 2017, now abandoned.

(30) Foreign Application Priority Data

Nov. 18, 2016  (JP) .............................. JP2016-225501

(51) Int. Cl.
*A61B 1/00* (2006.01)
*A61B 1/045* (2006.01)
(Continued)

(52) U.S. Cl.
CPC .... *A61B 1/000095* (2022.02); *A61B 1/00149* (2013.01); *A61B 1/045* (2013.01);
(Continued)

(58) Field of Classification Search
CPC .......... A61B 1/000095; A61B 1/00149; A61B 1/045; G06T 5/40; H04N 5/2256; H04N 2005/2255
(Continued)

(56) References Cited

U.S. PATENT DOCUMENTS 4,967,340 A * 10/1990 Dawes ................ G06F 15/8015
                                                          712/19
6,602,186 B1 * 8/2003 Sugimoto .......... G02B 23/2484
                                                          600/478
(Continued)

FOREIGN PATENT DOCUMENTS

JP    5-344524 A    12/1993
JP    2001-137187 A    5/2001
(Continued)

*Primary Examiner* — Sath V Perungavoor
*Assistant Examiner* — Kristin Dobbs
(74) *Attorney, Agent, or Firm* — Xsensus LLP

(57) ABSTRACT

A medical signal processing apparatus processes image signals input from an imaging device. The image signals corresponds to a result of examining a subject, and the imaging device sequentially outputs the image signals from multiple pixels arrayed in a matrix according to a raster to the medical signal processing apparatus. The medical image signal processing apparatus includes: a signal divider configured to divide the image signals according to the raster sequentially output from the imaging device into first divided image signals each according to a pixel group consisting of multiple pixels arrayed in connected multiple columns; and a plurality of pre-processors configured to process, in parallel, sets of pixel information of the multiple first divided image signals divided by the signal divider.

10 Claims, 8 Drawing Sheets

(51) Int. Cl.
  *G06T 5/40* (2006.01)
  *H04N 5/225* (2006.01)
(52) U.S. Cl.
  CPC ............ *G06T 5/40* (2013.01); *H04N 5/2256* (2013.01); *H04N 2005/2255* (2013.01)
(58) Field of Classification Search
  USPC .......................................................... 348/65
  See application file for complete search history.

(56) References Cited

U.S. PATENT DOCUMENTS

| | | | | |
|---|---|---|---|---|
| 2003/0007561 | A1* | 1/2003 | Kajiwara | ............... H04N 19/59 375/E7.065 |
| 2012/0299967 | A1* | 11/2012 | Urabe | ....................... G06T 1/20 345/660 |
| 2016/0063680 | A1* | 3/2016 | Ries | ....................... G09G 5/393 345/649 |

FOREIGN PATENT DOCUMENTS

| | | | |
|---|---|---|---|
| JP | 2010-51531 | A | 3/2010 |
| JP | 2011-24901 | A | 2/2011 |
| JP | 2012-34934 | A | 2/2012 |
| JP | 2015-96920 | A | 5/2015 |
| JP | 2016-10497 | A | 1/2016 |
| WO | 2009/142021 | A1 | 11/2009 |
| WO | 2015/163171 | A1 | 10/2015 |

* cited by examiner

MEDICAL SIGNAL PROCESSING APPARATUS AND MEDICAL OBSERVATION SYSTEM

CROSS-REFERENCE TO RELATED APPLICATIONS

This application is a continuation of U.S. application Ser. No. 15/808,106, filed Nov. 9, 2017, which claims priority to Japanese Patent Application No. 2016-225501 filed on Nov. 18, 2016, the entire contents of each are incorporated herein by reference.

BACKGROUND

The present disclosure relates to a medical signal processing apparatus and a medical observation system including the medical signal processing apparatus.

In the field of medicine, medical observation systems that image the inside of a subject, such a human being, (the inside of a living body) and observes the inside of the living body have been known (see Japanese Laid-open Patent Publication No. 2010-51531).

The medical observation system (endoscope system) according to Japanese Laid-open Patent Publication No. 2010-51531 includes an endoscope that is inserted into a living body and images the inside of the living body and then outputs image signals (raw data); a processor device that processes the image signals from the endoscope and generates video signals for display; and a monitor that displays images based on the video image signals generated by the processor device.

The processor device temporarily stores the image signals that are output from the endoscope in a memory (an image data memory) and then performs various types of processing on the image signals that are read from the memory.

SUMMARY

The volume of data of image signals that are output from a recent endoscope is relatively large (for example, high-definition image signals having a 4K resolution (hereinafter, 4K) or higher).

Dealing with such high-definition image signals of 4K or higher has a problem in that the processing load is excessive when, as in the case of the medical observation system according to Japanese Laid-open Patent Publication No. 2010-51531, the image signal is temporarily stored in the memory and then various types of processing are performed on the image signals that are read from the memory.

Under the circumstances, there is a need for a technique enabling reduction of the load of processing executed on the image signals that are read from the memory after being stored in the memory.

There is a need for a medical signal processing apparatus and a medical observation system enabling reduction of the load of processing executed on image signals read from a memory after being stored in the memory.

There is provided a medical signal processing apparatus for processing image signals input from an imaging device, the image signals corresponding to a result of examining a subject, and the imaging device sequentially outputting the image signals from multiple pixels arrayed in a matrix according to a raster to the medical signal processing apparatus, the medical image signal processing apparatus including: a signal divider configured to divide the image signals according to the raster sequentially output from the imaging device into first divided image signals each according to a pixel group consisting of multiple pixels arrayed in connected multiple columns; and a plurality of pre-processors configured to process, in parallel, sets of pixel information of the multiple first divided image signals divided by the signal divider.

DETAILED DESCRIPTION

Figure 1:
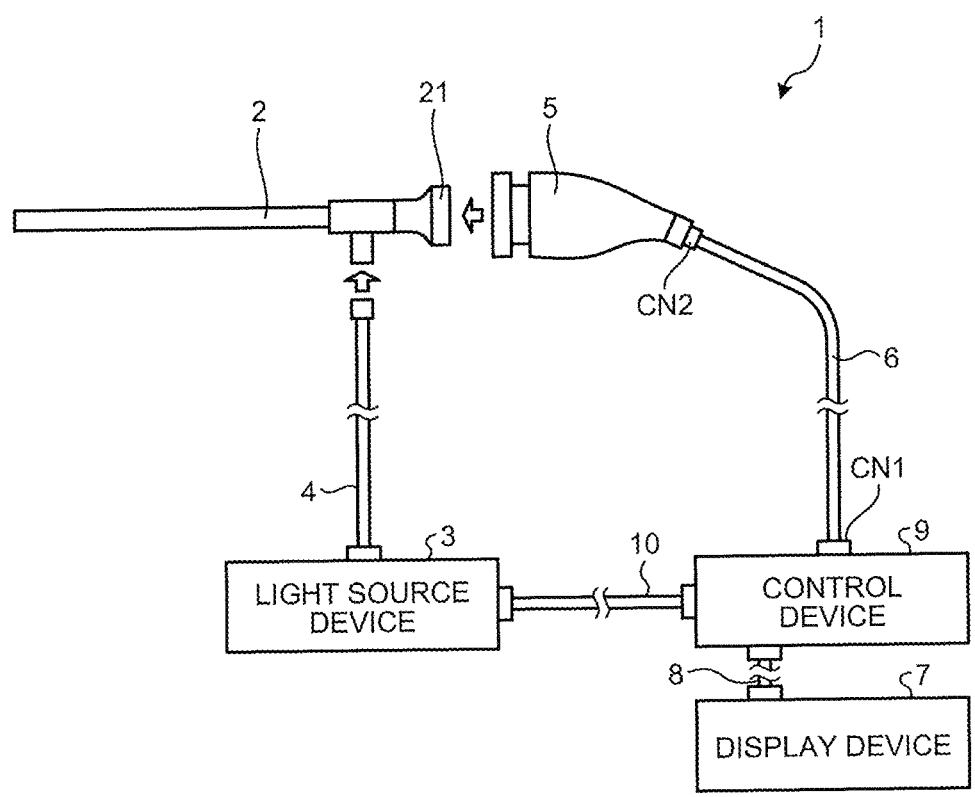
FIG. 1 is a diagram illustrating a schematic configuration of a medical observation system according to a first embodiment.

Modes for carrying out the present disclosure (hereinafter, embodiments) will be described below with reference to the accompanying drawings. The embodiments to be described below do not limit the present disclosure. The same components illustrated in the drawings are denoted with the same reference numbers.

First Embodiment

Schematic Configuration of Medical Observation System

FIG. 1 is a diagram illustrating a schematic configuration of a medical observation system 1 according to a first embodiment.

The medical observation system 1 is an apparatus that is used in the field of medicine and that observes a subject, such as the inside of a living body. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

The insertion unit 2 has a function serving as the endoscope according to the present disclosure. In the first embodiment, the insertion unit 2 includes a rigid endoscope. In other words, the insertion unit 2 is rigid or partly soft and is elongated. The insertion unit 2 is inserted into a living body. An optical system that includes at least one lens and focuses light of a subject image is provided in the insertion unit 2.

An end of the light guide 4 is connected to the light source device 3. Under the control of the control device 9, the light source device 3 supplies light for illuminating the inside of the living body to the end of the light guide 4.

The end of the light guide 4 is detachably connected to the light source device 3 and the other end of the light guide 4 is detachably connected to the insertion unit 2. The light guide 4 transmits the light supplied from the light source device 3 to the other end and supplies the light to the insertion unit 2. The light supplied to the insertion unit 2 is emitted from the tip of the insertion unit 2 and applied the inside of the living body. The light applied to the inside of the living body (a subject image) is focused by the optical system in the insertion unit 2.

The camera head 5 has a function serving as the imaging device according to the present disclosure. The camera head 5 is detachably connected to the base end of the insertion unit 2 (an eyepiece 21 (FIG. 1)). Under the control of the control device 9, the camera head 5 captures the subject image of which light is focused in the insertion unit 2 and outputs image signals (raw signals) obtained by the image capturing. In the first embodiment, the image signal is an image signal of 4K or higher.

The detailed configuration of the camera head 5 will be described below.

One end of the first transmission cable 6 is detachably connected to the control device 9 via a connector CN1 (FIG. 1) and the other end of the first transmission cable 6 is detachably connected to the camera head 5 via a connector CN2 (FIG. 1). The first transmission cable 6 transmits the image signals that are output from the camera head 5 to the control device 9 and transmits each of control signals, synchronization signals, clocks and power to the camera head 5.

The image signal may be transmitted from the camera head 5 to the control device 9 via the first transmission cable 6 by using an optical signal. Alternatively, the image signal may be transmitted by using an electric signal. This applies also to transmission of a control signal, a synchronization signal or a clock from the control device 9 to the camera head 5 via the first transmission cable 6.

The display device 7 includes a display for which, for example, liquid crystals or organic electro luminescence (EL) is used. The display device 7 displays an image based on the video image signal that is processed by the control device 9.

One end of the second transmission cable 8 is detachably connected to the display device 7 and the other end of the second transmission cable 8 is detachably connected to the control device 9. The second transmission cable 8 transmits the video image signal that is processed by the control device 9 to the display device 7.

The control device 9 has a function serving as the medical signal processing apparatus according to the present disclosure. The control device 9 includes a central processing unit (CPU) and controls operations of the light source device 3, the camera head 5, and the display device 7 across-the-board.

The detailed configuration of the control device 9 will be described below.

One end of the third transmission cable 10 is detachably connected to the light source device 3 and the other end of the third transmission cable 10 is detachably connected to the control device 9. The third transmission cable 10 transmits the control signal from the control device 9 to the light source device 3.

Configuration of Camera Head

The configuration of the camera head 5 will be described.

Figure 2:
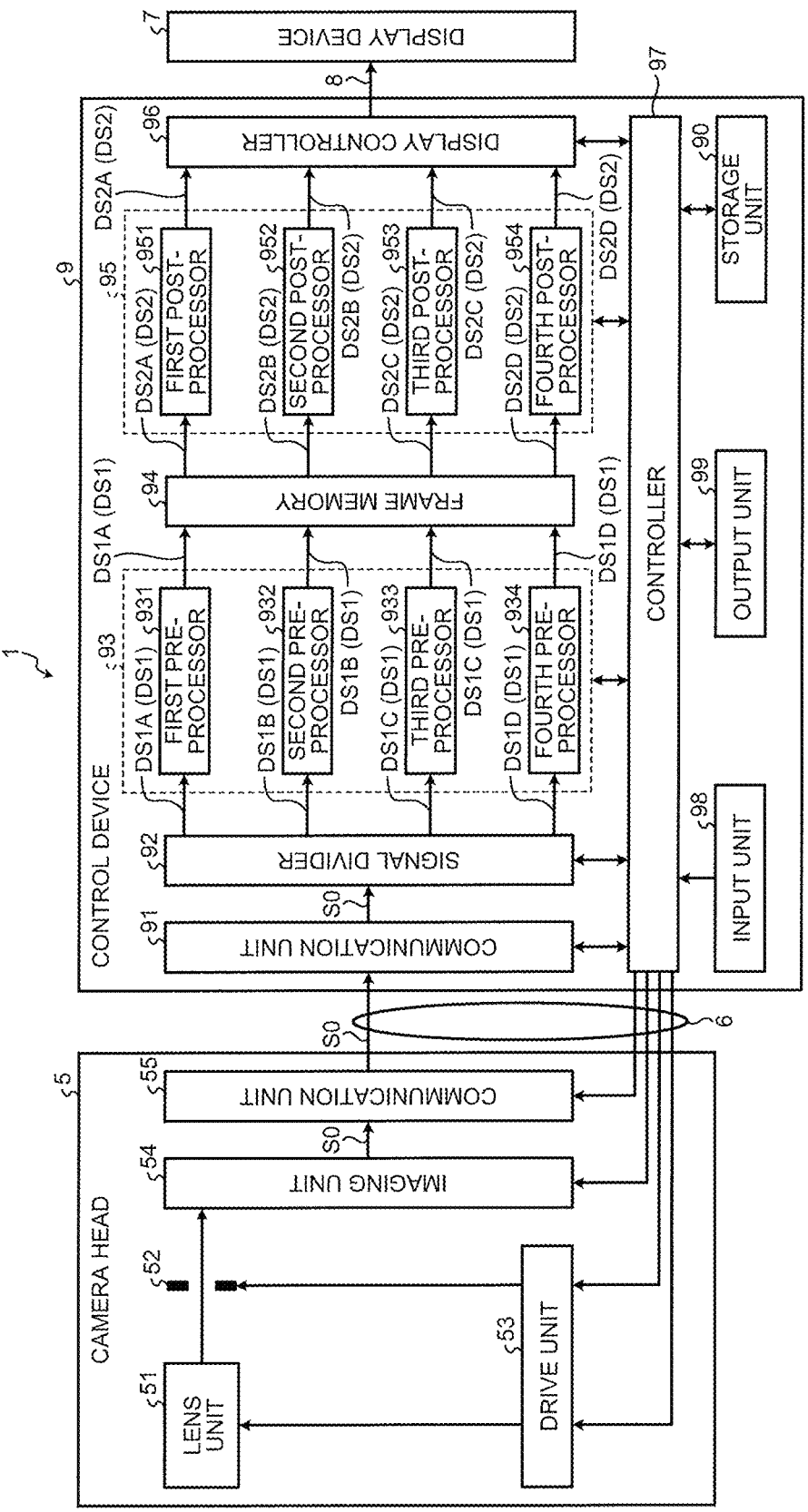
FIG. 2 is a block diagram illustrating a configuration of the camera head and the control device illustrated in FIG. 1.

FIG. 2 is a block diagram illustrating the configurations of the camera head 5 and the control device 9.

For the purpose of illustration, FIG. 2 does not illustrate the connector CN 1 between the control device 9 and the first transmission cable 6, the connector CN 2 between the camera head 5 and the first transmission cable 6, the connector between the control device 9 and the second transmission cable 8, and the connector between the display device 7 and the second transmission cable 8.

As illustrated in FIG. 2, the camera head 5 includes a lens unit 51, an iris 52, a drive unit 53, an imaging unit 54 and a communication unit 55.

The lens unit 51 includes at least one lens movable along an optical axis. The lens unit 51 forms the subject of which light is focused in the insertion unit 2 on the imaging surface of the imaging unit 54. In the lens unit 51, an optical zoom mechanism (not illustrated in the drawings) that changes the angle of view by moving at least one lens and a focus mechanism (not illustrated in the drawings) that changes the focal point are provided.

The iris 52 adjusts the exposure by limiting the amount of incident light focused by the lens unit 51.

Under the control of the control device 9, the drive unit 53 causes the optical zoom mechanism and the focus mechanism, which are described above, to operate to change the angle of view and the focal point of the lens unit 51. The drive unit 53 drives the iris 52 under the control of the control device 9 to adjust the amount of light incident on the imaging unit 54.

The imaging unit 54 images the inside of the living body under the control of the control device 9. The imaging unit 54 includes a sensor chip in which, for example, an imaging device 541 (see FIG. 3), such as a charge coupled device (CCD) or a complementary metal oxide semiconductor (CMOS) that receives the light of the subject image focused in the insertion unit 2 and formed by the lens unit 51 and that converts the light into electric signals, and a signal processor (not illustrated in the drawings) that performs image processing (A/D conversion) on the electric signals (analog signal) from the imaging device 541 and outputs image signals S0 (FIG. 2) are formed integrally. The imaging unit 54 outputs the image signals S0 (digital signal) having undergone A/D conversion. The above-described signal processor (not illustrated in the drawings) may be independent without being formed integrally with the imaging device 541.

Figure 3:
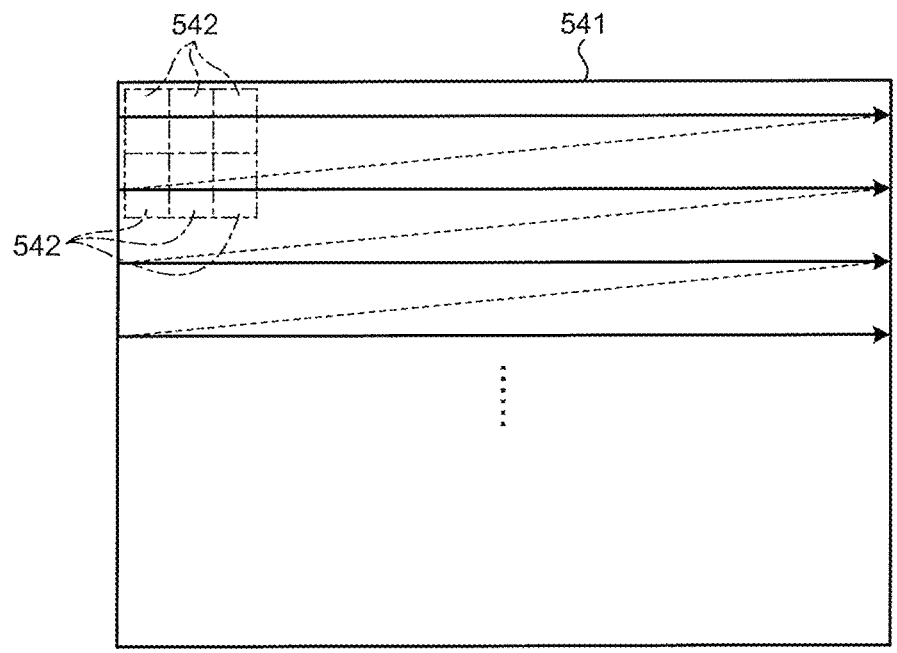
FIG. 3 is a diagram illustrating image signals that are output from the imaging unit illustrated in FIG. 2.

FIG. 3 is a diagram illustrating the image signals S0 that are output from the imaging unit 54. Specifically, FIG. 3 is a diagram schematically illustrating physical arrangement of each pixel 542 in the imaging device 541.

For the purpose of illustration, FIG. 3 illustrates only pixels 542 that are part of all the pixels in the imaging device 541.

As illustrated in FIG. 3, the imaging unit 54 sequentially outputs the image signals S0 having undergone A/D conversion according to a raster. Specifically, in the imaging device 541, the pixels 542 are arrayed in a matrix. As indicated by the arrows and dotted lines, the imaging unit 54 sequentially outputs the image signals S0 from the pixel 542 arrayed in the first column in the first row of the pixels 542 to the pixel 542 arrayed in the last column. The imaging unit 54 then sequentially outputs the image signals S0 from the pixels 542 in the second row from the pixel 542 arrayed in the first column to the pixel 542 arrayed in the last column. By continuing the above-described processing to the last row, the imaging unit 54 outputs the image signals S0 corresponding to one frame. To output the image signals S0 corresponding to the following frame, the imaging unit 54 returns to the pixels 542 in the first row and performs the same processing as that described above.

The communication unit 55 functions as a transmitter that transmits the image signals S0 according to the raster that are sequentially output from the imaging unit 54 to the control device 9 via the first transmission cable 6. According to the first embodiment, the communication unit 55 includes a high-speed serial interface that communicates the image signals S0 with the control device 9 via the first transmission cable 6 at a transmission rate of 1 Gbps or higher.

Configuration of Control Device

A configuration of the control device 9 will be described with reference to FIG. 2.

As illustrated in FIG. 2, the control device 9 includes a communication unit 91, a signal divider 92, a plurality of pre-processors 93, a frame memory 94, a plurality of post-processors 95, a display controller 96, a controller 97, an input unit 98, an output unit 99, and a storage unit 90.

The communication unit 91 functions as a receiver that receives the image signals S0 according to the raster, which are sequentially output from the camera head 5 (the communication unit 55) via the first transmission cable 6. In the first embodiment, the communication unit 91 includes a high-speed serial interface that communicates the image signals S0 at a transfer rate of 1 Gbps or higher with the communication unit 55.

The signal divider 92 divides the image signals S0 according to the raster, which are output sequentially from the camera head 5 (the communication unit 55) via the first transmission cable 6 and the communication units 55 and 91, into first divided image signals DS1 (FIG. 2) each according to each pixel group consisting of multiple pixels that are arrayed in connected multiple columns.

Figure 4:
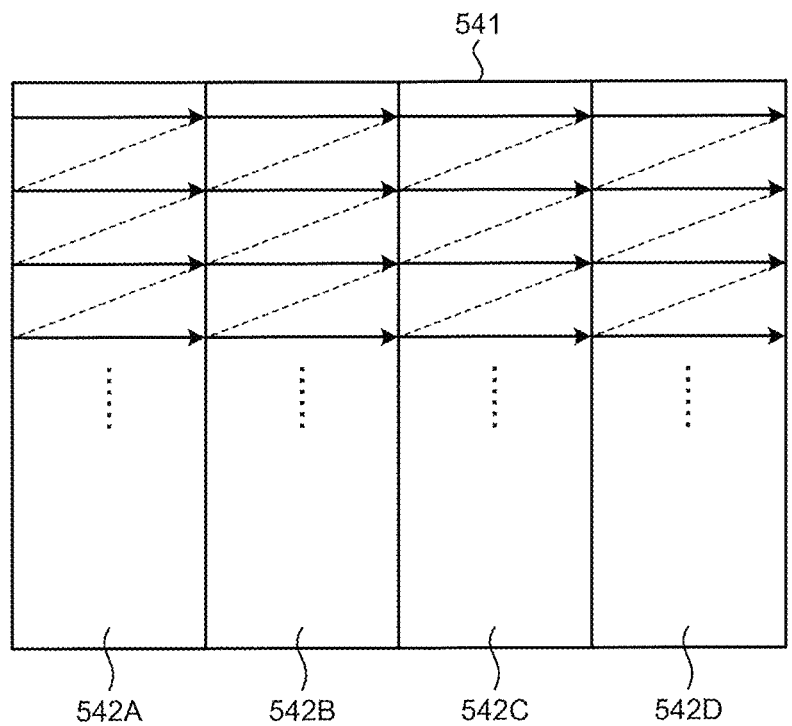
FIG. 4 is a diagram illustrating first divided image signals resulting from signal division performed by the signal divider illustrated in FIG. 2.

FIG. 4 is a diagram illustrating first divided image signals DS1 (DS1A to DS1D) resulting from signal division performed by the signal divider 92.

FIG. 4 is a diagram corresponding to FIG. 3; however, for the purpose of illustration, each pixel 542 is not illustrated in FIG. 4. In FIG. 4, all pixels in the imaging device 541 are segmented into first to fourth pixel groups 542A to 542D. The first pixel group 542A consists of multiple pixels 542 arrayed in a stripe area obtained by connecting the predetermined number of columns from the first column. The second pixel group 542B consists of the multiple pixels 542 arrayed in a stripe area obtained by connecting the predetermined number of columns from the column to the immediate right of the first pixel group 542A. The third pixel group 542C consists of the multiple pixels 542 arrayed in a stripe area obtained by connecting the predetermined number of columns from the column to the immediate right of the second pixel group 542B. The fourth pixel group 542D consists of the multiple pixels 542 arrayed in a stripe area obtained by connecting the predetermined number of columns from the column to the immediate right of the third pixel group 542C to the last column.

The above-described predetermined number of columns in the first to fourth pixel groups 542A to 542D may be the same between at least two of the first to fourth pixel groups 542A to 542D or may be different among all the first to fourth pixel groups 542A to 542D.

Specifically, as indicated by the arrows and dotted lines in FIG. 4, the signal divider 92 regards, among the image signals S0 that are output from the pixels 542 in the first row, the image signals S0 that are output from the first pixel group 542A as a first divided image signal DS1A (FIG. 2), the image signals S0 that are output from the second pixel group 542B as a first divided image signal DS1B (FIG. 2), the image signals S0 that are output from the third pixel group 542C as a first divided image signal DS1C (FIG. 2), and the image signals S0 that are output from the fourth pixel group 542D as a first divided image signal DS1D (FIG. 2). In the same manner, with respect to the image signals S0 that are output from the pixels 542 in the second row, the signal divider 92 regards the image signals S0 that are output from the first to fourth pixel groups 542A to 542D as first divided image signals DS1A to DS1D. By continuing the above-described processing until the last row, the signal divider 92 divides the image signals S0 corresponding to one frame into the four first divided image signals DS1A to DS1D.

The number of groups into which the image signals S0 are divided by the signal divider 92 is not limited to four as long as the signal divider 92 is configured to divide the image signals, which are input according to the raster, into first divided image signals DS1 each according to the unit of a pixel group consisting of multiple pixels that are arrayed in connected multiple columns, and the number may be any other number.

The same number of the pre-processors 93 as the number of groups into which the image signals S0 are divided by the signal divider 92 are provided. In other words, in the first embodiment, the pre-processors 93 include four first to fourth pre-processors 931 to 934 as illustrated in FIG. 2. The first to fourth pre-processors 931 to 934 process sets of pixel information of the four first divided image signals DS1A to DS1D in parallel.

For example, the first to fourth pre-processors 931 to 934 execute, in parallel, sets of detection processing for controlling the camera head 5 (lens control, such as auto focus (AF) or automatic exposure control (AE)) according to sets of pixel information of the four first divided image signals DS1A to DS1D. Furthermore, according to the sets of pixel information of the four first divided image signals DS1A to DS1D, the first to fourth pre-processors 931 to 934 execute, in parallel, sets of detection processing for calculating operation parameters used in part of image processing (such as optical black subtraction processing or white balance adjustment processing) performed by the post-processors 95.

The sets of processing executed in parallel by the pre-processors 93 are not limited to the above-described processing. Any processing may be executed as long as it is part of various types of processing executed on image signals corresponding to one frame that are read from the frame memory after being stored in the frame memory 94.

The following processing may be exemplified as detection processing for executing AE and lens control and detection processing for executing calculation of operation parameters used in the white balance adjustment processing.

For example, when the first divided image signal DS1A is focused, the first pre-processor 931 executes detection of frequency components, detection of an area average value or a maximum and minimum pixels with, for example, a filter, determination made by comparison with a threshold, and detection of, for example, a histogram.

Figure 5:
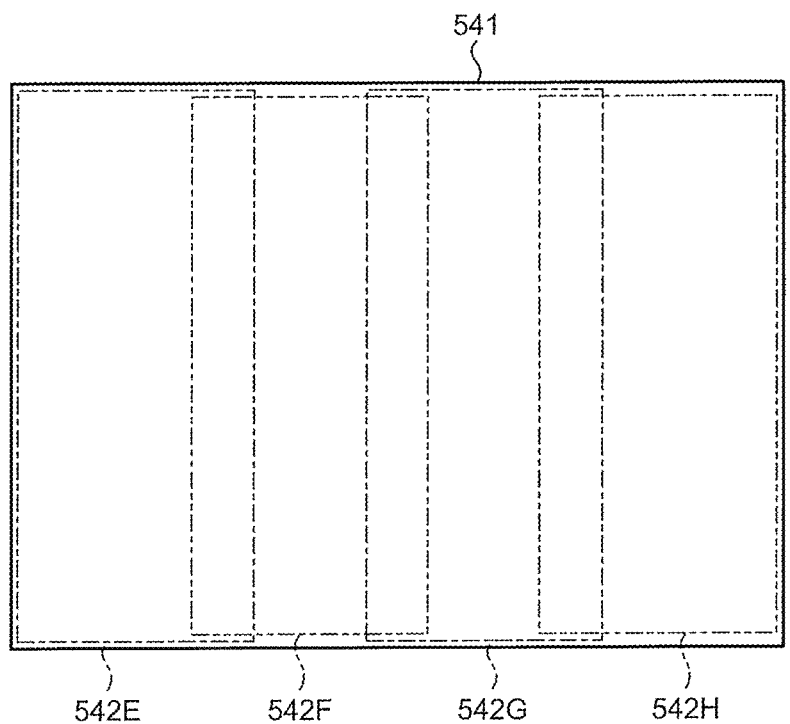
FIG. 5 is a diagram illustrating second divided image signals that are read by the first to fourth post-processors illustrated in FIG. 2.

When a filter is used, the first to fourth pixel groups 542A to 542D may be pixel groups having an overlap between adjacent pixel groups (for example, fifth to eighth pixel groups 542E to 542H illustrated in FIG. 5).

Optical black (OPB) detection to be described below may be exemplified as the detection processing for executing calculation of operation parameters used in optical black subtraction processing.

For example, each of the first to fourth pre-processors 931 to 934 integrates sets of pixel information in the OPB area around valid pixels in the imaging device 541.

Each of the first to fourth pre-processors 931 to 934 then outputs the detection information obtained by performing the detection processing to the controller 97.

The frame memory 94 has a function serving as the memory according to the disclosure. The frame memory 94 sequentially stores the four first divided image signals DS1A to DS1D after execution of the above-described detection processing by the first to fourth pre-processors 931 to 934 to store the image signals 0 corresponding to one frame.

The post-processors 95 respectively read multiple second divided image signals DS2 (FIG. 2) of different multiple areas in a whole image area of the image signals S0 corresponding to one frame and stored in the frame memory 94 and execute sets of image processing in parallel. In the first embodiment, the post-processors 95 include four first to fourth post-processors 951 to 954 as illustrated in FIG. 2.

FIG. 5 is a diagram illustrating the second divided image signals DS2 (DS2A to DS2D) that are read by the first to fourth post-processors 951 to 954 from the frame memory 94.

For the purpose of illustration, FIG. 5 represents the whole image area of the image signals S0 corresponding to one frame and stored in the frame memory 94 by using all the pixels in the imaging device 541 in association with FIG. 4. In FIG. 5, all the pixels in the imaging device 541 are segmented into fifth to eighth pixel groups 542E to 542H. The fifth pixel group 542E consists of the multiple pixels 542 arrayed in a stripe area obtained by connecting the predetermined number of columns from the first column. The sixth pixel group 542F consists of the multiple pixels 542 arrayed in a stripe area obtained by connecting the predetermined number of columns from a column in the fifth pixel group 542E. The seventh pixel group 542G consists of the multiple pixels 542 arrayed in a stripe area obtained by connecting the predetermined number of columns from a column in the sixth pixel group 542F. The eighth pixel group 542H consists of the multiple pixels 542 arrayed in a stripe area obtained by connecting only given columns from a column in the seventh pixel group 542G to the last column.

In other words, pixel groups adjacent to each other among the first to eighth pixel groups 542E to 542H have an overlap.

The above-described predetermined number of columns in the fifth to eighth pixel groups 542E to 542H may be the same between at least two of the fifth to eighth pixel groups 542E to 542H or may be different among all the fifth to eighth pixel groups 542E to 542H.

Specifically, the first post processor 951 reads, as the second divided signal DS2A (FIG. 2), the image signals S0 that are output from the fifth pixel group 542E among the pixel signals S0 corresponding to one frame and stored in the frame memory 94. The second post processor 952 reads, as the second divided image signal DS2B (FIG. 2), the image signals S0 that are output from the sixth pixel group 542F among the image signals S0 corresponding to one frame and stored in the frame memory 94. Furthermore, the third post processor 953 reads, as the second divided image signal DS2C (FIG. 2), the image signals S0 that are output from the seventh pixel group 542G among the image signals S0 corresponding to one frame and stored in the frame memory 94. The fourth post processor 954 reads, as the second divided image signal DS2D (FIG. 2), the image signals S0 that are output from the eighth pixel group 542H among the image signals S0 corresponding to one frame and stored in the frame memory 94.

The first to fourth post-processors 951 to 954 then uses the operation parameters that are output from the controller 97 to execute, in parallel, sets of image processing, such as optical black subtraction processing, demosaic processing, white-balance adjustment processing, noise reduction, color correction, color enhancement and contour enhancement, on the read four second divided image signals DS2A to DS2D.

The display controller 96 generates a video image signal for display without the above-described overlapped areas from the four second divided image signals DS2A to DS2D after execution of the image processing by the first to fourth post-processors 951 to 954 and outputs the video image signal to the display device 7 via the second transmission cable 8. The display device 7 then displays an image based on the video image signal for display.

The controller 97 includes, for example, a CPU. The controller 97 outputs control signals via the first and third transmission cables 6 and 10 to control operations of the light source device 3, the drive unit 53, the imaging unit 54, and the communication unit 55 and controls entire operations of the control device 9.

Specifically, the controller 97 adjusts the angle of view and the focal point of the lens unit 51 by controlling the operations of the drive unit 53 according to the detection information that is output from the first to fourth pre-processors 931 to 934 (lens control). The controller 97 drives the iris 52 and adjusts the interval of electronic shuttering by the imaging unit 54 and the gain (AE) by controlling the operations of the drive unit 53 according to the detection information. The controller 97 calculates operation parameters used in part of the image processing performed by the first to fourth post-processors 951 to 954 (for example, optical black subtraction processing and white balance adjustment processing) according to the detection information and outputs the operation parameters to the first to fourth post-processors 951 to 954. For example, the controller 97 averages the accumulated values of the sets of pixel information on the OPB area obtained by performing the optical black detection performed by the first to fourth pre-processors 931 to 934 and uses the average values as operation parameter used in optical black subtraction processing performed by the first to fourth post-processors 951 to 954.

The input unit 98 includes operation devices, such as a mouse, a keyboard and a touch panel and accepts operations of the user.

The output unit 99 includes, for example, a speaker and a printer. The output unit 99 outputs various types of information.

The storage unit 90 stores a program that is executed by the controller 97, information necessary for processing performed by the controller 97, etc.

The control device 9 according to the first embodiment described above produces the following effects.

The control device 9 according to the first embodiment includes the signal divider 92 that divides the signals S0 that are output from the camera head 5 into the four first divided image signals DS1A to DS1D and the four first to fourth pre-processors 931 to 934 that process the sets of pixel information of the four first divided image signals DS1A to DS1D.

Accordingly, it is possible to execute, before the image signals S0 are stored in the frame memory 94, part of various types of processing that used to be executed on the image signals S0 read from the frame memory 94 after being stored in the frame memory 94. Thus, the control device 9 according to the first embodiment produces an effect that it is possible to reduce the load of the processing executed on the image signals S0 read from the frame memory 94 after being stored in the frame memory 94 (the load of processing performed by the post-processors 95).

Particularly, the image signals S0 that are output sequentially according to the raster are divided into the four first divided image signals DS1A to DS1D and sets of pixel information of the four first divided image signals DS1A to DS1D are processed in parallel. Thus, it is possible to promptly execute the processing on the image signals S0 having a relatively large amount of data of 4K or larger.

The control device 9 according to the first embodiment divides the image signals S0 that are output sequentially according to the raster into the first divided image signals DS1A to DS1D respectively according to the pixel groups 542A to 542D each consisting of the multiple pixels 542 arrayed in connected multiple columns and processes, in parallel, sets of pixel information of the four first divided image signals DS1A to DS1D. In other words, as the delay corresponding to only the difference between 1-line readings occurs at each set of timing at which the pixel information of each of the four first divided image signals DS1A to DS1D is processed, it is possible to sufficiently derive the effect of parallel processing.

In the control device 9 according to the first embodiment, the first to fourth pre-processors 931 to 934 execute sets of detection processing for controlling the camera head 5 (lens control or AE) in parallel according to the sets of pixel information of the four first divided image signals DS1A to DS1D.

For this reason, for example, in comparison with the configuration in which the detection processing is executed on the image signals S0 that are read from the frame memory 94 after being stored in the frame memory 94, it is possible to execute the detection processing before the image signals S0 are stored in the frame memory 94 and therefore it is possible to execute lens control and AE promptly.

In the control device 9 according to the first embodiment, the first to fourth pre-processors 931 to 934 execute, in parallel, sets of detection processing for calculating operation parameters used in part of the image processing performed by the post-processors 95 (for example, optical black subtraction processing or white balance adjustment processing) according to the sets of pixel information of the four first divided image signals DS1A to DS1D.

Accordingly, for example, in comparison with the configuration in which the detection processing is executed on the image signals S0 that are read from the frame memory 94 after being stored in the frame memory 94, it is possible to execute the detection processing before the image signals S0 are stored in the frame memory 94 and therefore it is possible to reduce the load of the processing performed by the post-processors 95 and reduce the latency in the image processing performed by the post-processors 95.

The control device 9 according to the first embodiment further includes the frame memory 94 that sequentially stores the four first divided image signals DS1A to DS1D and stores the image signals S0 corresponding to one frame and the four first to fourth post-processors 951 to 954 that read the four second divided image signals DS2A to DS2D, respectively, from the frame memory 94 and that execute, in parallel, sets of image processing on the four second divided image signals DS2A to DS2D. In other words, as in the case of the processing at the former stage before the storing in the frame memory 94 (the processing performed by the first to fourth pre-processors 931 to 934), the processing at the latter stage after the storing in the frame memory 94 (the processing performed by the first to fourth post-processors 951 to 954) is also performed as parallel processing. For this reason, it is possible to promptly execute sets of processing at the former and latter stages on the image signals S0 having a relatively large amount of data of 4K or higher.

It is also assumed that the signal divider 92 and the first to fourth pre-processors 931 to 934 are provided not in the control device 9 but in the camera head 5. Such a configuration has a risk that the following problem occurs.

The camera head 5 is a part held by a hand of a technologist. For this reason, the camera head 5 is required to be small and light. In other words, providing the signal divider 92 and the first to fourth pre-processors 931 to 934 to the camera head 5 has a problem in that reduction in the size and weight of the camera head 5 is hindered. Furthermore, there is a problem of a risk that, due to the heat generated by the signal divider 92 and the first to fourth pre-processors 931 to 934 according to the use, the temperature of the camera head 5 exceeds a predetermined limit of temperature.

On the other hand, in the medical observation system 1 according to the first embodiment, the signal divider 92 and the first to fourth pre-processors 931 to 934 are divided in the control device 9 and therefore the above-described problem does not occur.

When the processing performed by the signal divider 92 and the first to fourth pre-processors 931 to 934 is light, it is unnecessary to pay attention to reduction in size and weight and heat generation, and therefore the camera head 5 may be provided without provision of the signal divider 92 and the first to fourth pre-processors 931 to 934 to the control device 9.

Second Embodiment

A second embodiment of the present disclosure will be described here.

In the following descriptions, the same components as those of the above-described first embodiment will be denoted with the same reference numbers as those in the first embodiment and detailed descriptions thereof will be omitted or simplified.

Figure 6:
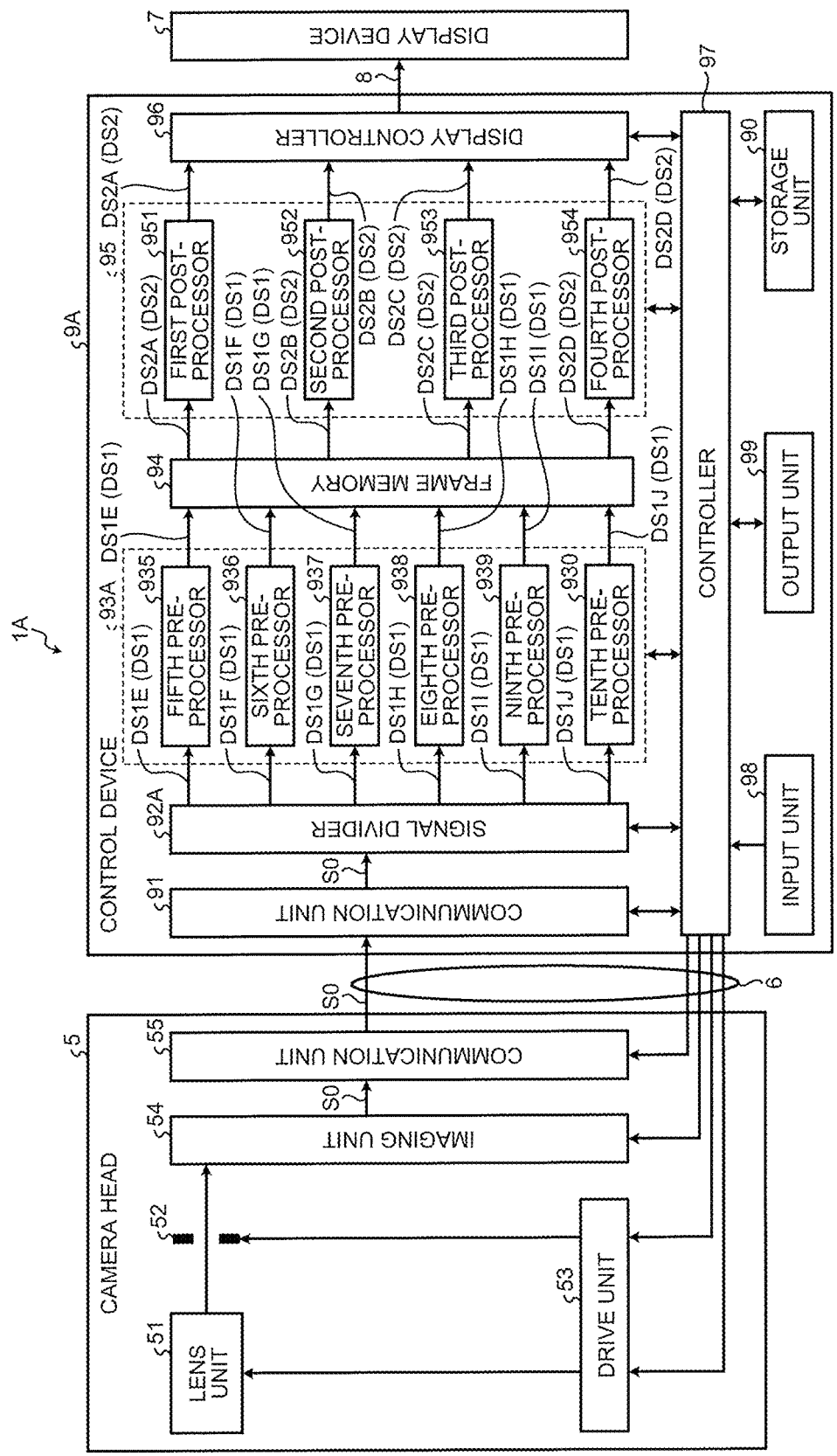
FIG. 6 is a diagram corresponding to FIG. 2 and illustrating a schematic configuration of a medical observation system according to a second embodiment.

FIG. 6 is a diagram corresponding to FIG. 2. FIG. 6 is a diagram illustrating a schematic configuration of a medical observation system 1A according to the second embodiment.

The medical observation system 1A (a control device 9A) according to the second embodiment is different from the medical observation system 1 (the control device 9) in the way the signal divider 92A corresponding to the signal divider 92 divides the image signals S0 and in the configuration of a plurality of pre-processors 93A corresponding to the pre-processors 93 (the control device 9) according to the above-described embodiment.

Figure 7A:
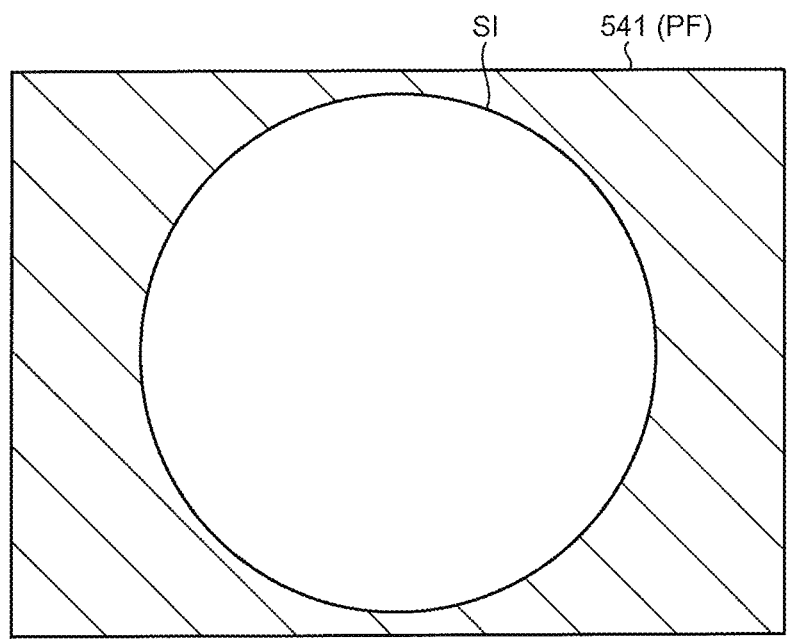
FIG. 7A is a diagram illustrating first divided image signals resulting from signal division performed by the signal divider illustrated in FIG. 6.
Figure 7B:
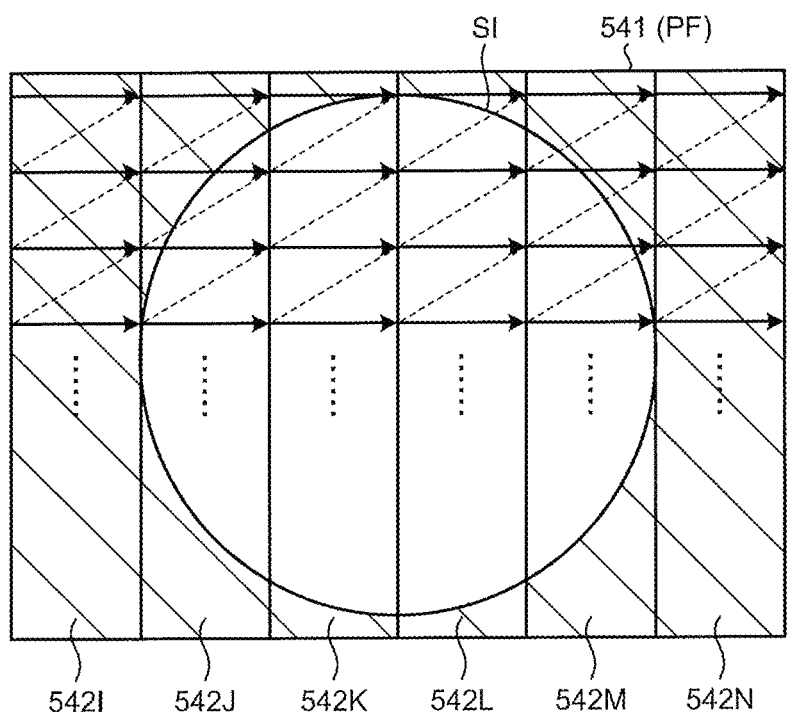
FIG. 7B is a diagram illustrating the first divided image signals resulting from signal division performed by the signal divider illustrated in FIG. 6.

FIGS. 7A and 7B are diagrams illustrating first divided image signals DS1 (DS1E to DS1J) resulting from signal division performed by the signal divider 92A.

For the purpose of illustration, FIGS. 7A and 7B represent a captured image PF containing a subject image SI captured by the imaging unit 54 in all pixels in the imaging device 541 in association with FIG. 4.

The subject image SI in the captured image PF captured by the imaging unit 54 is approximately circular as illustrated in FIG. 7A or FIG. 7B. For this reason, in the whole area of the captured image PF, the area other than the subject image SI (the hatched area in FIGS. 7A and 7B) is an unnecessary area.

In FIG. 7B, for the purpose of illustration, all the pixels in the imaging device 541 are divided into ninth to fourteenth pixel groups 542I to 542N. The ninth pixel group 542I consists of the multiple pixels 542 arrayed in a stripe area obtained by connecting columns from the first column to the column serving as an approximate tangent of the subject image SI. The tenth pixel group 542J consists of the multiple pixels 542 arrayed in a stripe area obtained by connecting the predetermined number of columns from the column to the immediate right of the ninth pixel group 542I. The eleventh pixel group 542K consists of the multiple pixels 542 arrayed in a stripe area obtained by connecting the predetermined number of columns from the column to the immediate right of the tenth pixel group 542J. The twelfth pixel group 542L consists of the multiple pixels 542 arrayed in a stripe area obtained by connecting the predetermined number of columns from the column to the immediate right of the eleventh pixel group 542K. The thirteenth pixel group 542M consists of the multiple pixels 542 arrayed in a stripe area obtained by connecting the predetermined number of columns from the column to the immediate right of the twelfth pixel group 542L to the column serving as an approximate tangent of the subject image SI. The fourteenth pixel group 542N consists of the multiple pixels 542 arrayed in a stripe area obtained by connecting the predetermined number of columns from the column to the immediate right of the thirteenth pixel group 542M to the last column.

The above-described predetermined number of columns in the tenth to thirteenth pixel groups 542J to 542M may be the same between at least two of the tenth to thirteenth pixel groups 542J to 542M or may be different among all the tenth to thirteenth pixel groups 542J to 542M.

Specifically, the signal divider 92A according to the second embodiment regards, among the image signals S0 that are output from the pixels 542 of the first row, the image signals S0 output from the ninth pixel group 542I as a first divided image signal DS1E (FIG. 6), the image signals S0 output from the tenth pixel group 542J as a first divided image signal DS1F (FIG. 6), the image signals S0 output from the eleventh pixel group 542K as a first divided image signal DS1G (FIG. 6), the image signals S0 output from the twelfth pixel group 542L as a first divided image signal DS1H (FIG. 6), the image signals S0 output from the thirteenth pixel group 542M as a first divided image signal DS1I (FIG. 6), and the image signals S0 output from the fourteenth pixel group 542N as a first divided image signal DS1J (FIG. 6). With respect to the image signals S0 that are output from the pixels 542 of the second row, the signal divider 92A then regards the image signals S0 output from the ninth to fourteenth pixel groups 542I to 542N as first divided image signals DS1E to DS1J, respectively. The signal divider 92A continues the above-described processing to the last row, thereby dividing the image signals S0 corresponding to one frame into six first divided image signals DS1E to DS1J.

The number of groups into which the image signals S0 are divided by the signal divider 92A is not limited to six as long as there are four or more groups including the two first divided image signals DS1E and DS1J, and the image signals S0 may be divided into another number of groups.

The same number of the pre-processors 93A as the number of groups into which the image signals S0 are divided by the signal divider 92A are provided. In other words, according to the second embodiment, the pre-processors 93A include the six fifth to tenth pre-processors 935 to 939 and 930. The fifth and tenth pre-processors 935 and 930 remove two first divided image signals DS1E AND DS1J. The sixth to ninth pre-processors 936 to 939 execute the same processing as that performed by the first to fourth pre-processors 931 to 934 according to the above-described first embodiment. The four first divided image signals DS1F to DS1I after being processed by the sixth to ninth pre-processors 936 to 939 are sequentially stored in the frame memory 94.

According to the control device 9A according to the second embodiment, the unnecessary area other than the subject image SI in the captured image PF is removed in the processing at the former stage before the storing in the frame memory 94 (by the processing performed by the signal divider 92A and the fifth and tenth pre-processors 935 and 930). For this reason, the image signals having a small amount of data is processed in the processing at the latter stage after the storing in the frame memory 94 (by the first to fourth post-processors 951 to 954). This enables reduction of the load of the processing at the latter stage (the load of the processing performed by the first to fourth post-processors 951 to 954).

Third Embodiment

A third embodiment of the present disclosure will be described.

In the following descriptions, the same components as those of the above-described first embodiment will be denoted with the same reference numbers as those in the first embodiment and detailed descriptions thereof will be omitted or simplified.

In the above-described first embodiment, the present disclosure is applied to the medical observation system 1 using the rigid endoscope (the insertion unit 2).

On the other hand, in the third embodiment, the present disclosure is applied to a medical observation system using a so-called video scope including an imaging unit on the tip of an insertion unit.

Figure 8:
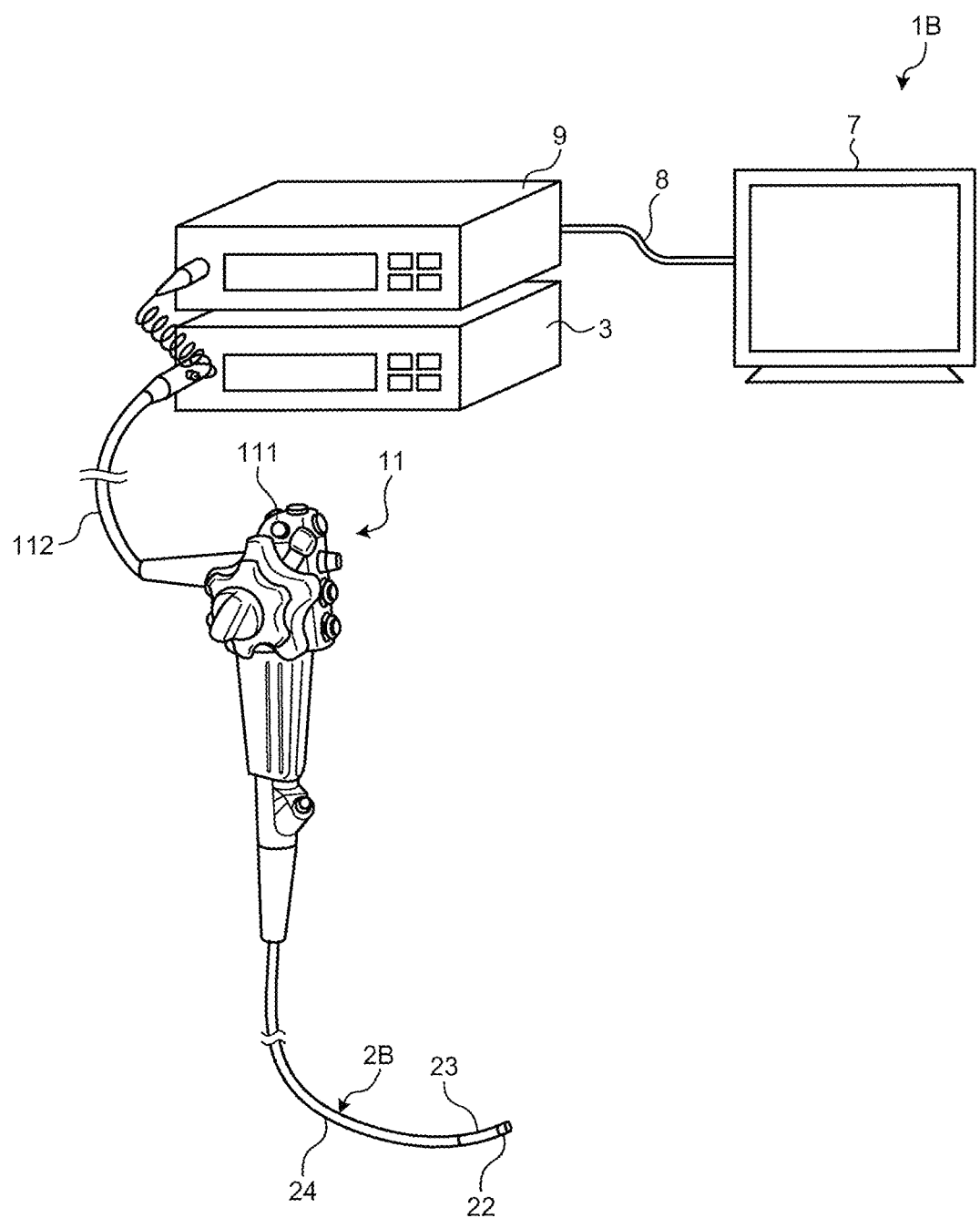
FIG. 8 is a diagram illustrating a schematic configuration of a medical observation system according to a third embodiment.

FIG. 8 is a diagram illustrating a schematic configuration of a medical observation system 1B according to the third embodiment.

As illustrated in FIG. 8, the medical observation system 1B according to the third embodiment includes an endoscope 11 that inserts its insertion unit 2B into a living body to capture internal images of a site to be observed and outputs the image signals S0; the light source device 3 that generates illumination light emitted from the tip of the endoscope 11; the control device 9 that processes the image signals S0 that are output from the endoscope 11; and the display device 7 that is connected to the control device 9 via the second transmission cable 8 and displays an image based on a video image that is processed by the control device 9.

As illustrated in FIG. 8, the endoscope 11 includes the insertion unit 2B that is flexible and elongated; an operation unit 111 that is connected to the base-end side of the insertion unit 2B and that receives inputs of various operation signals; and a universal cord 112 that extends in a direction different from a direction in which the insertion unit 2B extends from the operation unit 111 and incorporates various cables connected to the light source device 3 and the control device 9.

As illustrated in FIG. 8, the insertion unit 2B includes a tip 22, a curved part 23 that is connected to the base-end side of the tip 22, that includes multiple curved pieces and that may be freely curved; and a flexible tube 24 that is connected to the base-end side of the curved part 23 and that is flexible and elongated.

Although not specifically illustrated in FIG. 8, the same components as the lens unit 51, the iris 52, the drive unit 53 and the imaging unit 54 according to the above-described first embodiment are incorporated in the tip 22. In other words, the endoscope 11 (the tip 22) has a function serving as the image capturing device according to the present disclosure. Although not specifically illustrated in FIG. 8, the same component as the communication unit 55 according to the above-described first embodiment is incorporated in the operation unit 111. The image signals S0 captured by the tip 22 (the imaging unit) are sequentially output according to the raster to the control device 9 via the operation unit 111 and the universal cord 112.

Even when the soft endoscope (the endoscope 11) is used as in the above-described third embodiment, the same effects as those according to the first embodiment are produced.

Fourth Embodiment

A fourth embodiment of the present disclosure will be described.

In the following descriptions, the same components as those of the above-described first embodiment will be denoted with the same reference numbers as those in the first embodiment and detailed descriptions thereof will be omitted or simplified.

In the above-described first embodiment, the present disclosure is applied to the medical observation system 1 using the rigid endoscope (the insertion unit 2).

On the other hand, in the fourth embodiment, the present disclosure is applied to a medical observation system using an operation endoscope that captures images while enlarging a given view area of the inside of a subject (the inside of a living body) or the surface of the subject (the surface of the living body).

Figure 9:
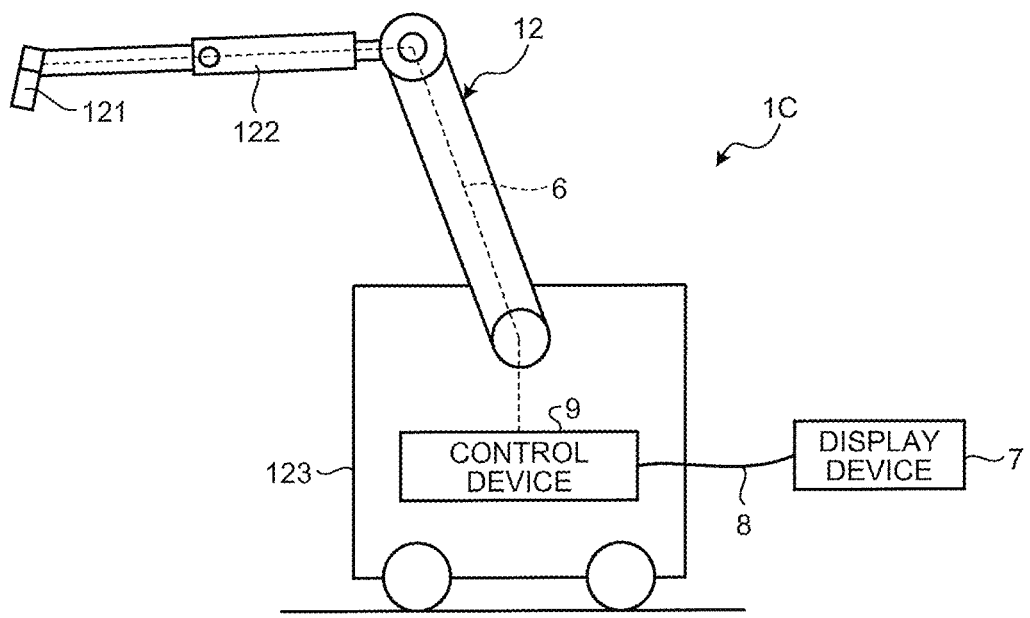
FIG. 9 is a diagram illustrating a schematic configuration of a medical observation system according to a fourth embodiment.

FIG. 9 is a diagram illustrating a schematic configuration of a medical observation system 1C according to the fourth embodiment.

As illustrated in FIG. 9, the medical observation system 1C according to the fourth embodiment includes an operation endoscope 12 that captures images for observing a subject and outputs the image signals S0, the control device 9 that processes the image signals S0 that are output from the operation endoscope 12, and the display device 7 that is connected to the control device 9 via the second transmission cable 8 and that displays an image based on a video signal that is processed by the control device 9.

As illustrated in FIG. 9, the operation endoscope 12 includes an endoscope unit 121 that enlarges a fine site of the subject and images the fine site and that outputs the image signals S0; a supporter 122 that is connected to the base end of the endoscope unit 121 and that includes an arm rotatably supporting the endoscope unit 121; and a base unit 123 that rotatably holds the base end of the supporter 122 and that is movable on a floor surface.

As illustrated in FIG. 9, the control device 9 is set on the base unit 123.

The base unit 123 may be configured not to be provided movably on the floor surface but to be fixed on a ceiling or a wall surface to support the supporter 122. The base unit 123 may include a light source unit that generates illumination light that is emitted to the subject from the operation endoscope 12.

Although not specifically illustrated in FIG. 9, the same components as the lens unit 51, the iris 52, the drive unit 53, the imaging unit 54 and the communication unit 55 according to the above-described first embodiment are incorporated in the endoscope unit 121. In other words, the operation endoscope 12 (the endoscope unit 121) has a function serving as the imaging device according to the present disclosure. The image signals S0 captured by the endoscope unit 121 (the imaging unit) are sequentially output according to the raster to the control device 9 via the wired first transmission cable 6 along the supporter 122.

Even when the operation endoscope 12 is used as in the above-described fourth embodiment, the same effects as those of the first embodiment are produced.

Other Embodiments

The embodiments for carrying out the present disclosure have been described; however, the present disclosure should not be limited only by the above-described first to four embodiments.

Figure 10:
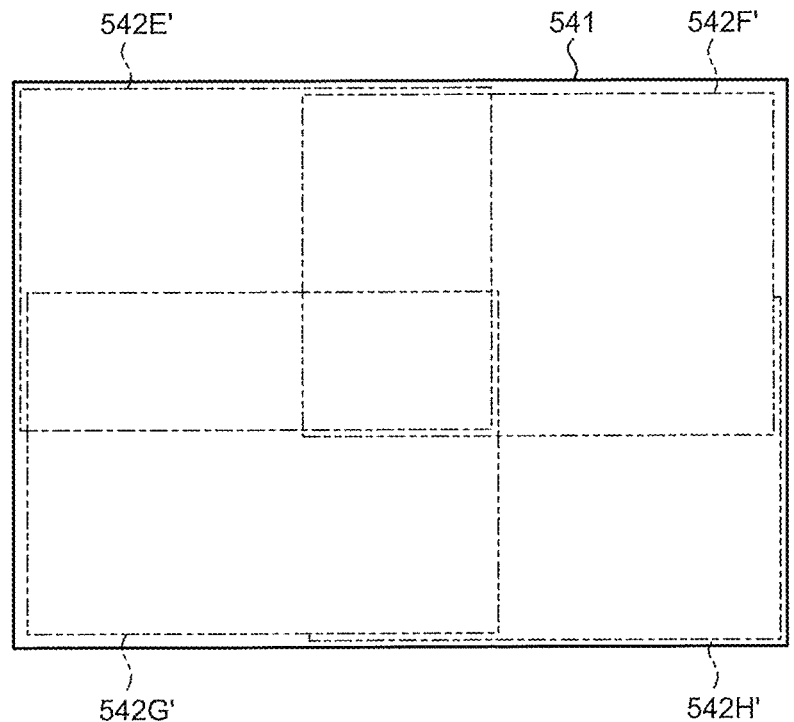
FIG. 10 is a diagram illustrating a modification of the first to fourth embodiments.

FIG. 10 is a diagram illustrating a modification of the first to fourth embodiments. Specifically, FIG. 10 is a diagram corresponding to FIG. 5.

According to FIG. 10, all the pixels in the imaging device 541 are divided into fifth to eighth pixel groups 542E' to 542H'. The fifth pixel group 542E' consists of the multiple pixels 542 arrayed in a rectangular area containing only the upper-left corner among the four corners of the screen. The sixth pixel group 542F' consists of the multiple pixels 542 arrayed in a rectangular area containing only the upper-right corner among the four corners of the screen. The seventh pixel group 542G' consists of the multiple pixels 542 arrayed in a rectangular area containing only the lower-left corner among the four corners of the screen. The eighth pixel group 542H' consists of the multiple pixels 542 arrayed in a rectangular area containing only the lower-right corner among the four corners on the screen.

The fifth to eighth pixel groups 542E' to 542H' have overlaps.

In the above-described first to fourth embodiments, the first to fourth post-processors 951 to 954 read, among the image signals S0 corresponding to one frame stored in the frame memory 94, the image signals S0 from the fifth to eighth pixel groups 542E to 542H as the second divided image signals DS2A to DS2D; however, the embodiments are not limited thereto and, for example, the image signals S0 may be read as described below.

The first post processor 951 reads, among the image signals S0 corresponding to one frame and stored in the frame memory 94, the image signals S0 that are output from the fifth pixel group 542E' (FIG. 10) as a second divided image signal DS2A. The second post processor 952 reads, among the image signals S0 corresponding to one frame and stored in the frame memory 94, the image signals S0 that are output from the sixth pixel group 542F' (FIG. 10) as a second divided image signal DS2B. The third post processor 953 reads, among the image signals S0 corresponding to one frame and stored in the frame memory 94, the image signals S0 that are output from the seventh pixel group 542G' (FIG. 10) as a second divided image signal DS2C. The fourth post processor 954 reads, among the image signals S0 corresponding to one frame and stored in the frame memory 94, the image signals S0 that are output from the eighth pixel group 542H' (FIG. 10) as a second divided image signal DS2D.

In the first to fourth embodiments, the signal dividers 92 and 92A may be provided outside the control device 9. For example, the signal divider 92 may be provided to the camera head 5, the connector CN1 or CN2, the endoscope 11, or the operation endoscope 12. The same applies to the pre-processors 93 and 93A.

In the above-described first to fourth embodiments, instead of the frame memory 94, a line memory that sequentially stores only the image signals S0 corresponding to one line according to the raster may be used.

In the above-described first to fourth embodiments, the frame memory 94 sequentially stores the multiple first divided image signals DS1 via the signal divider 92 or 92A and the pre-processor 93 or 93A; however, the embodiments are not limited thereto. For example, a configuration in which the image signals S0 according to the raster are output from the communication unit 91 to the frame memory 94 in addition to the signal divider 92 or 92A may be employed. In other words, the frame memory 94 sequentially stores the image signals S0 according to the raster that are output from the communication unit 91 not via the signal divider 92 or 92A and the pre-processor 93 or 93A.

The first to fourth embodiments may employ a configuration in which light adjustment control on the light source device 3 is executed according to the detection processing executed by the pre-processors 93 or the pre-processors 93A.

A medical signal processing apparatus according to the present disclosure includes: a signal divider that divides image signals that are output from an imaging device into multiple first divided image signals; and a plurality of pre-processors that processes sets of pixel information of the first divided image signals in parallel.

It is therefore possible to execute, before the image signals are stored in the memory, part of various types of processing that used to be executed on the image signals output from the imaging device, stored in a memory, and then read from the memory. Accordingly, the medical signal processing apparatus according to the present disclosure produces an effect that it is possible to reduce the load of the processing executed on the image signals that are read from the memory after being stored in the memory.

Particularly, the image signals that are output sequentially according to the raster are divided into the multiple first divided image signals and sets of pixel information of the multiple first divided image signals are processed in parallel. Thus, it is possible to promptly execute the processing on the image signals having a relatively large amount of data of, for example, 4K or larger.

The case where image signals that are output from the imaging device are divided into four divided image signals by performing so-called square-division and sets of pixel information of the four divided image signals are processed in parallel has the following problem.

The square-division refers to division of all pixels arrayed in a matrix into four areas along an approximate center row and an approximate center column serving as boundaries among all the rows and columns, and image signals from the pixels arrayed in the areas serve as divided image signals.

In other words, the image signals are output from the imaging device according to the raster. For this reason, in the square-division, a delay occurs between the timing at which the pixel information of the divided image signal on the upper side of the screen is processed and the timing at which the pixel information of the divided image signal on the lower side of the screen and therefore it is not possible to obtain the effect of parallel processing.

On the other hand, according to the present disclosure, the image signals that are output sequentially according to the raster into the first divided image signals each according to each pixel group consisting of multiple pixels arrayed in connected multiple columns and sets of pixel information of the multiple first divided image signals are processed in parallel. In other words, as the delay corresponding to only the difference between 1-line readings occurs at each set of timing at which the pixel information of each of the multiple divided image signals is processed, it is possible to sufficiently derive the effect of parallel processing.

The medical observation system according to the present disclosure includes the above-described medical signal processing apparatus and thus produces the same function and effect as those of the above-described medical signal processing apparatus.

It should be understood by those skilled in the art that various modifications, combinations, sub-combinations and alterations may occur depending on design requirements and other factors insofar as they are within the scope of the appended claims or the equivalents thereof.

What is claimed is:

1. A medical signal processing apparatus for processing image signals of an image input from a camera, and the camera sequentially outputting the image signals of the image from multiple pixels arrayed in a matrix according to a raster to the medical signal processing apparatus, the medical image signal processing apparatus comprising:
   signal divider circuitry configured to divide the image signals of the image according to the raster sequentially output from the camera into divided image signals each according to a pixel group consisting of multiple pixels arrayed in connected multiple groups which do not overlap;
   a plurality of pre-processor circuitries configured to process, in parallel, sets of pixel information of the multiple divided image signals divided by the signal divider and to transmit the sets of pixel information in parallel that were processed in parallel;
   a memory to receive in parallel the sets of pixel information processed by the plurality of pre-processor circuitries and store in parallel as stored data the sets of pixel information processed by the plurality of pre-processor circuitries; and
   a plurality of post-processor circuitries to receive in parallel the stored data as sets of pixel information from the memory which includes the sets of pixel information processed in parallel by the plurality of pre-processor circuitries and execute, in parallel, image processing on the sets of pixel information from the memory, adjacent sets of the sets of pixel information from the memory overlapping each other.

2. The medical signal processing apparatus according to claim 1, wherein the processing performed by the pre-processor circuitries executes, in parallel, sets of detection processing for controlling the camera based on the sets of pixel information of the multiple divided image signals.

3. The medical signal processing apparatus according to claim 1, wherein the processing performed by the pre-processor circuitries executes, in parallel, sets of detection processing for calculating operation parameters used in image processing performed on the image signals based on the sets of pixel information of the multiple divided image signals.

4. The medical signal processing apparatus according to claim 1, wherein
the camera is configured to capture an image containing a subject image loaded by an endoscope,
the signal divider circuitry is configured to divide the image signals from multiple pixels corresponding to two unnecessary areas excluding the subject image in the captured image into two of the multiple divided image signals, and
the pre-processor circuitries are configured to remove the two divided image signals from the multiple pixels corresponding to the two unnecessary areas among the multiple divided signals and process, in parallel, the sets of pixel information of the multiple divided image signals excluding the two divided image signals.

5. A medical observation system comprising:
a camera configured to image a subject and sequentially output image signals from multiple pixels arrayed in a matrix according to a raster; and
the medical signal processing apparatus according to claim 1 configured to process the image signals according to the raster that are sequentially output from the camera.

6. A medical signal processing apparatus for processing image signals of an image input from a camera, and the camera sequentially outputting the image signals of the image from multiple pixels arrayed in a matrix according to a raster to the medical signal processing apparatus, the medical image signal processing apparatus comprising:
signal divider circuitry configured to divide the image signals of the image according to the raster sequentially output from the camera into divided image signals each according to a pixel group consisting of multiple pixels arrayed in connected multiple groups which do not overlap;
a plurality of means for pre-processing configured to process, in parallel, sets of pixel information of the multiple divided image signals divided by the signal divider and to transmit the sets of pixel information in parallel that were processed in parallel;
a memory to receive in parallel the sets of pixel information processed by the plurality of means for pre-processing and store in parallel as stored data the sets of pixel information processed by the plurality of means for pre-processing; and
a plurality of means for post-processing to receive in parallel the stored data as sets of pixel information from the memory which includes the sets of pixel information processed in parallel by the plurality of means for pre-processing and execute, in parallel, image processing on the sets of pixel information from the memory, adjacent sets of the sets of pixel information from the memory overlapping each other.

7. The medical signal processing apparatus according to claim 6, wherein the processing performed by the means for pre-processing executes, in parallel, sets of detection processing for controlling the camera based on the sets of pixel information of the multiple divided image signals.

8. The medical signal processing apparatus according to claim 6, wherein the processing performed by the means for pre-processing executes, in parallel, sets of detection processing for calculating operation parameters used in image processing performed on the image signals based on the sets of pixel information of the multiple divided image signals.

9. The medical signal processing apparatus according to claim 6, wherein
the camera is configured to capture an image containing a subject image loaded by an endoscope,
the signal divider circuitry is configured to divide the image signals from multiple pixels corresponding to two unnecessary areas excluding the subject image in the captured image into two of the multiple divided image signals, and
the means for pre-processing are configured to remove the two divided image signals from the multiple pixels corresponding to the two unnecessary areas among the multiple divided signals and process, in parallel, the sets of pixel information of the multiple divided image signals excluding the two divided image signals.

10. A medical observation system comprising:
a camera configured to image a subject and sequentially output image signals from multiple pixels arrayed in a matrix according to a raster; and
the medical signal processing apparatus according to claim 6 configured to process the image signals according to the raster that are sequentially output from the camera.

* * * * *